United States Patent [19]

Johns et al.

[11] Patent Number: 5,049,219
[45] Date of Patent: Sep. 17, 1991

[54] METHOD AND APPARATUS FOR MANUFACTURING SURGICAL SPONGES

[75] Inventors: Herman S. Johns, Hendersonville, N.C.; Charles A. Lee, Knoxville, Tenn.

[73] Assignee: DeRoyal Industries, Inc., Powell, Tenn.

[21] Appl. No.: 489,893

[22] Filed: Mar. 6, 1990

[51] Int. Cl.$^5$ .............................................. B32B 31/18
[52] U.S. Cl. ...................................... 156/73.1; 156/250; 156/263; 156/264; 156/265; 156/266; 156/510; 156/516; 156/522; 156/552; 156/580.1; 604/358; 604/362
[58] Field of Search .................... 156/73.1, 250, 263, 156/264, 265, 266, 510, 511, 516, 522, 580.1, 552; 604/358, 362, 369, 386

[56] References Cited

U.S. PATENT DOCUMENTS

| | | | |
|---|---|---|---|
| 2,597,884 | 5/1952 | Marks | 156/552 |
| 2,600,322 | 6/1952 | Raney | 156/552 |
| 2,601,005 | 6/1952 | Raney | 156/552 |
| 3,551,245 | 12/1970 | Gamberini | 156/265 |
| 4,154,640 | 5/1979 | Kenworthy | 156/552 |
| 4,227,960 | 10/1980 | Loeffler et al. | 156/552 |
| 4,378,261 | 3/1983 | Burns et al. | 156/265 |

Primary Examiner—Caleb Weston
Attorney, Agent, or Firm—Luedeka, Hodges, Neely & Graham

[57] ABSTRACT

A method and apparatus are described for the manufacture of surgical sponges defined by a sponge body with at least a segment of a string, preferably containing a material opaque to x-rays, joined to the sponge body. The apparatus provides for the manufacture of the surgical sponges in an automatic manner and continuous manner by feeding a length of the string from a string supply and an end portion of sponge from a supply of sponge in directions substantially ninety-degrees to one another to an area of intersection area where a segment of the string overlies the sponge at a selected distance from the end thereof remote to the supply of sponge. The string segment is joined to the sponge, preferably by an ultrasonic welding mechanism. The sponge end containing the joined string is then severed at a preselected location depending upon the width of sponge body desired. The cutting mechanism used to sever the sponge and the welding mechanism are moveable as a single unit to alternately place the welding mechanism over the segment of the string and cutting mechanism at the preselected location on the sponge. The sponge bodies serially connected by the string at spaced apart locations are separated into discrete surgical sponges by sequentially displacing the string-connected sponge bodies to a string and sponge cutting arrangement where the string is first cut at an edge of each sponge and then an excess of the sponge adjacent this edge of each sponge is severed.

35 Claims, 7 Drawing Sheets

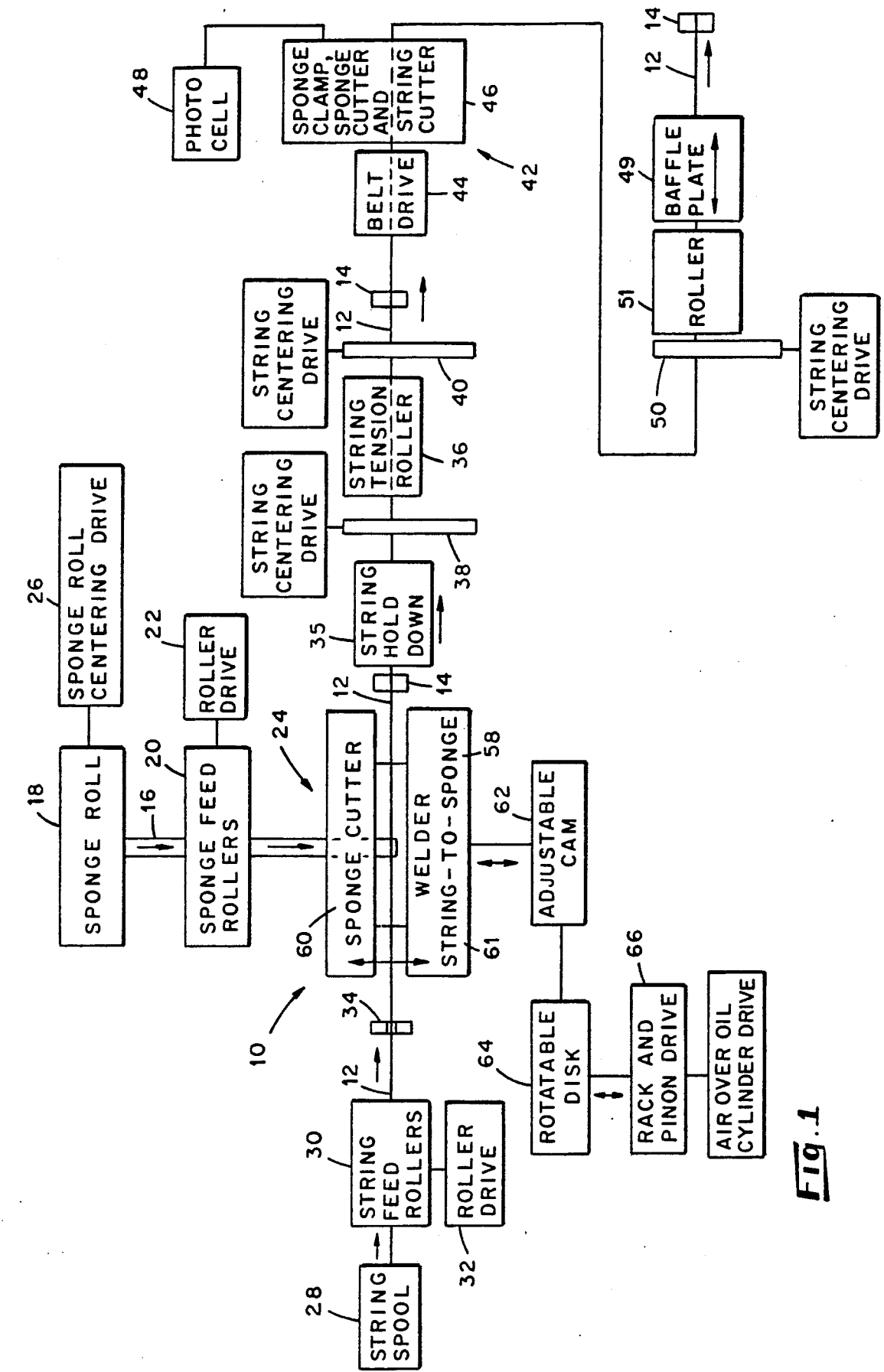

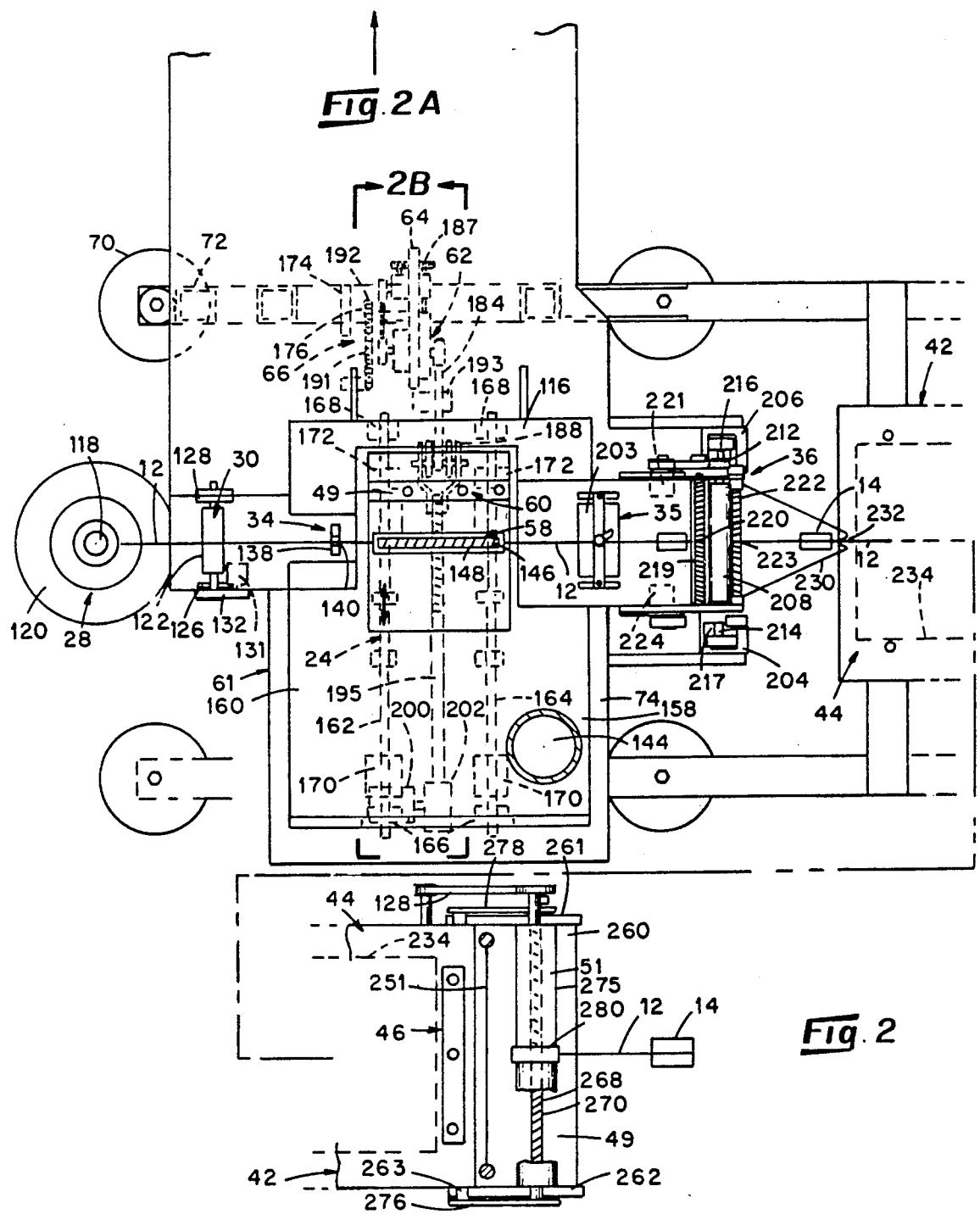

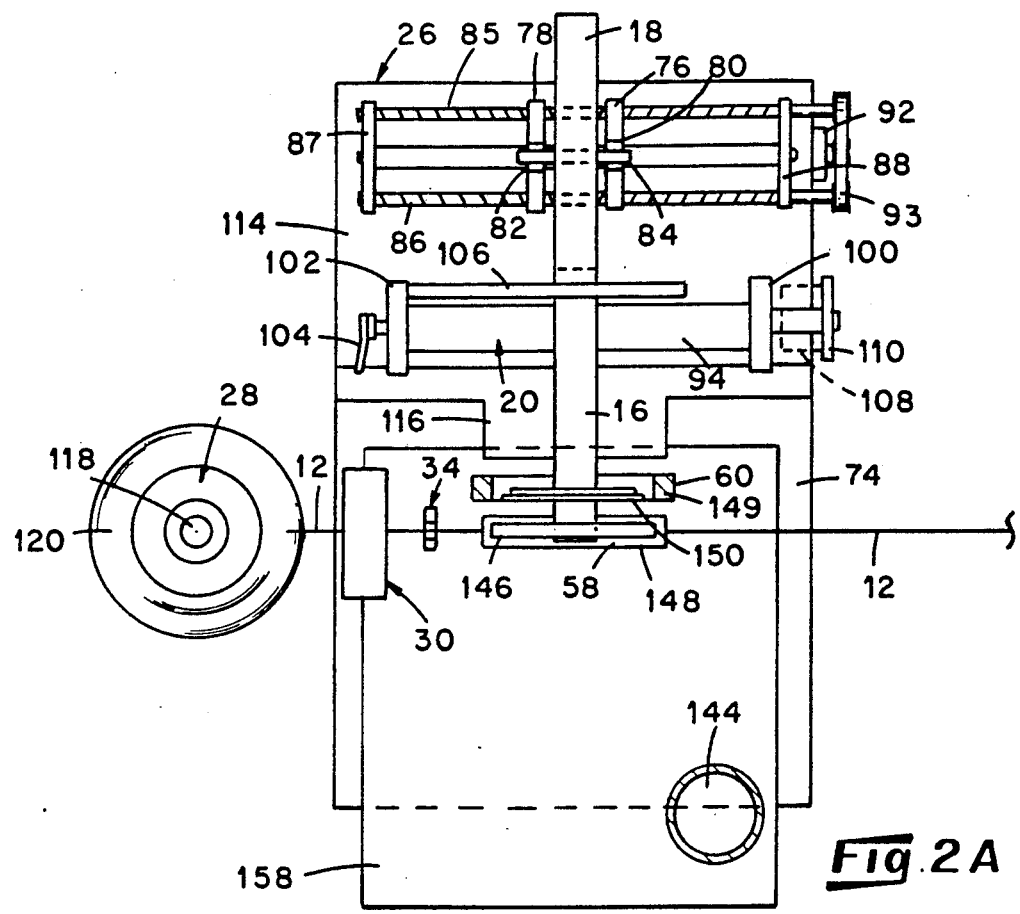
*Fig.2A*
*Fig.2*
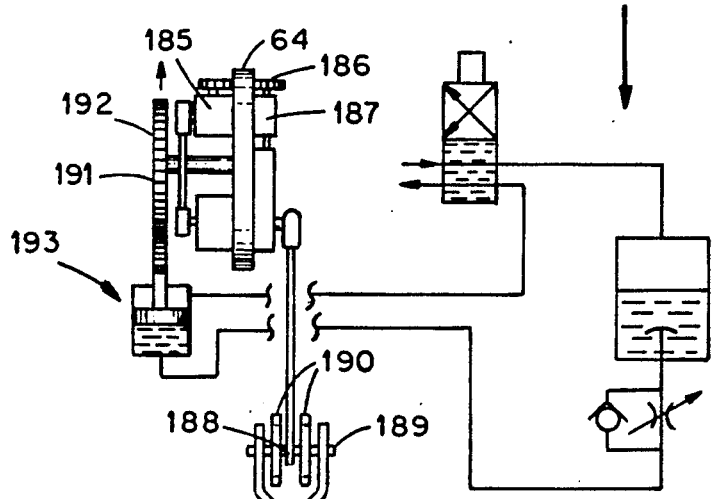
*Fig.2B*

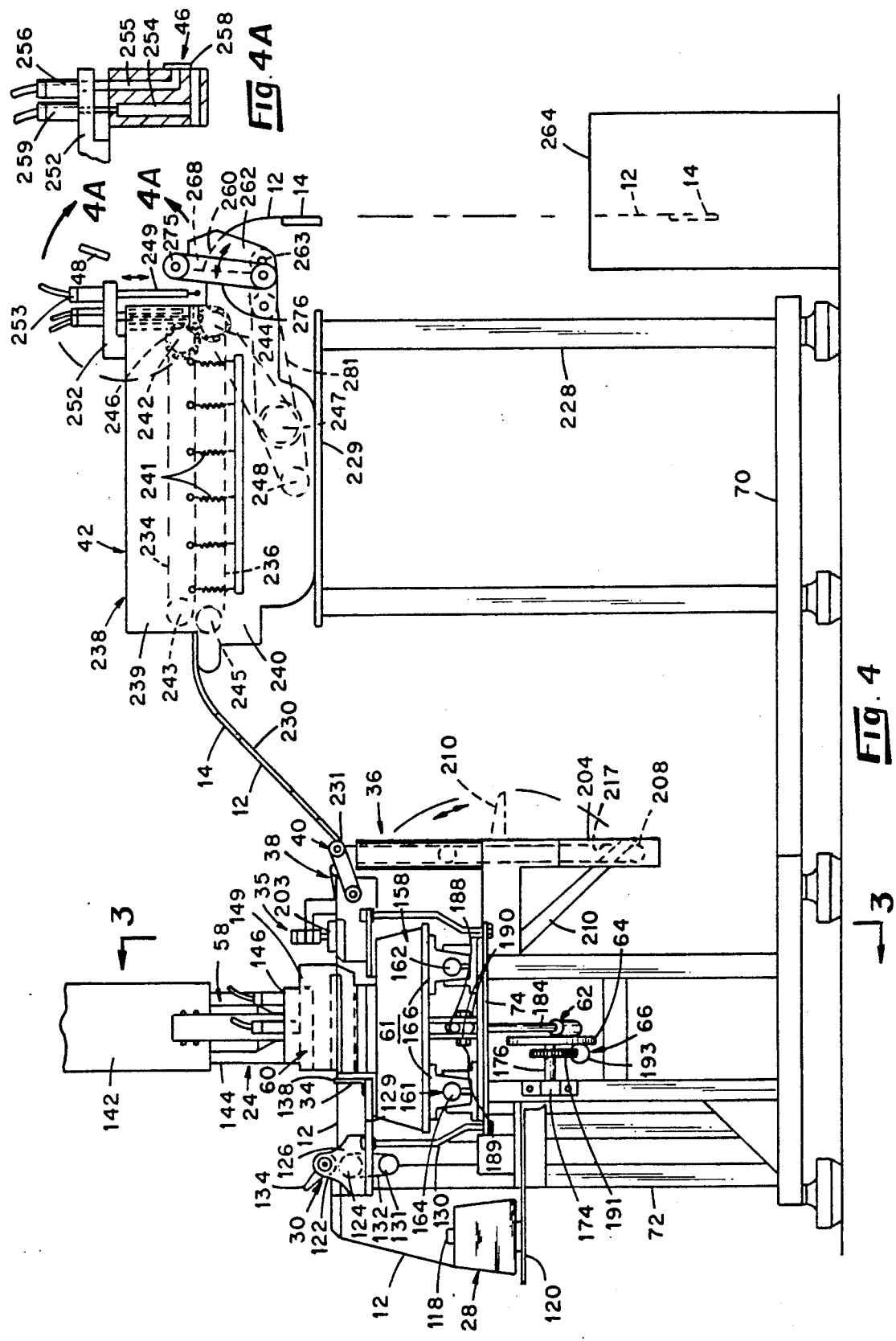

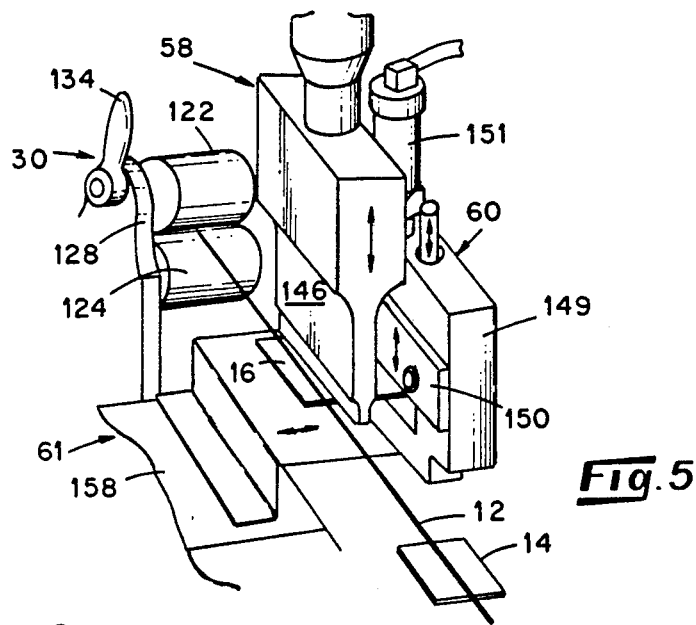
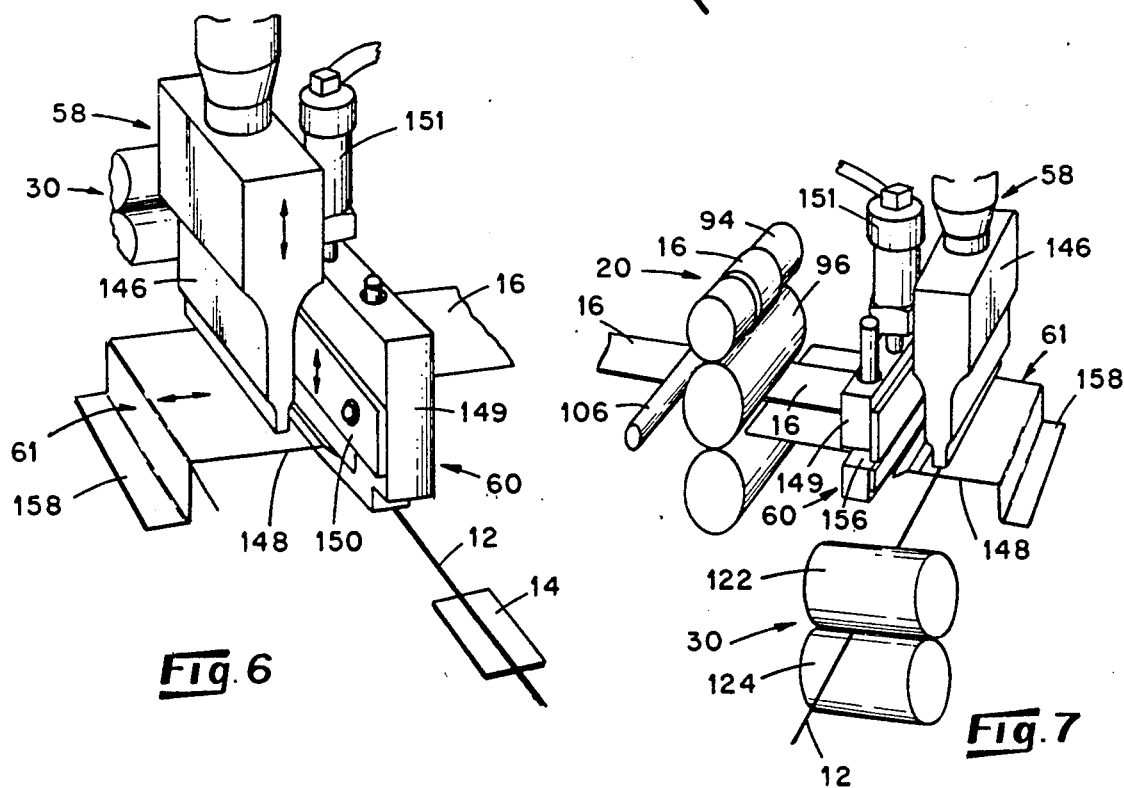

METHOD AND APPARATUS FOR MANUFACTURING SURGICAL SPONGES

BACKGROUND OF THE INVENTION

The present invention relates generally to manufacture of surgical sponges each formed of a fluid absorbing fibrous-web body with a string or thread, preferably containing material opaque to x-ray radiation, attached thereto. More particularly, the present invention is directed to the method and apparatus for automatically fabricating such surgical sponges, especially neurosurgical sponges, in a continuous manner.

Surgical sponges of various shapes and sizes have long been used in a myriad of surgical procedures for the absorption of blood and body fluids, packings and the like. The surgical sponges are frequently saturated with a saline solution or other solution for protecting tissue during the use of suction devices. Recent developments in the preparation of surgical sponges, particularly neurosurgical sponges, included the joining of a relatively long locator string or thread to a surface of the sponge body to facilitate locating and retrieval of the sponges from body cavities. These strings commonly project from the sponge body a distance of about 12 inches and incorporate a material which is opaque to radio waves in the x-ray band to facilitate the locating of the surgical sponges in body cavities.

The fibrous-web forming the body of the sponge is formed of highly absorbent fibrous material, such as rayon, in which the fibers are chemically and/or mechanically bonded into a mat-like construction which is characterized by minimal fiber loss during use. The sponge body can be of any desired thickness, commonly in the range of about 1.0 to about 3.00 millimeters in thickness, which is sufficient for fluid absorption, possesses adequate permeability for use with fluid suction devices, and is sufficiently pliable to serve as a tissue wipe. The sponge body has been formed in various configurations including round, oval, square or rectangular. The surgical sponges are available in various sizes are commonly in the range of about ¼ inch to about 6 inches in length and about ¼ inch to about 3½ inches in width.

The locator string joined to the sponge body is preferably formed of a bundle of elongated monofilaments, preferably of a polymeric thermoplastic material such as polypropylene, that have been impregnated with an x-ray opaque material such as barium sulfate. A sufficient number of monofilaments are incorporated in the bundle to assure that the string will be readily detectable during the use of a typical low-power portable x-ray unit as commonly utilized in surgical arenas. The bundle of monofilaments are, in turn, overwrapped with one or more layers of helically wound yarn, preferably fibrous, which serves to bind together the x-ray opaque monofilaments and enhance the tensile strength of the string. The yarn has been satisfactorily formed of medically acceptable materials such as cotton and various polyesters.

The joinder of the string to the sponge body has been achieved by attaching at least an end segment of the string to a surface of the sponge body by employing any suitable bonding technique capable of forming an adequately strong bond between the string and the sponge body. A preferred technique of achieving this joinder between the sponge body and the string is a heat-pressure bond provided by ultrasonic welding. The string is joined to the surface of the sponge over a cross-sectional length thereof which is adequate to assure the presence of a bond of sufficient integrity to remain intact during use of the surgical sponge. In the case of smaller surgical sponges, e.g., neurosurgical sponges, the bond between the string and the sponge body is preferably provided over essentially an entire length dimension of the sponge body. When using ultrasonic welding as the bonding technique, the string components, i.e., both the yarn overwrap and the monofilaments forming the encased bundle, are preferably formed of thermoplastic materials so that they jointly contribute to the formation of the bond with the sponge body.

Further and more specific details pertaining to surgical sponges, including neurosurgical sponges, are set forth in assignee's copending U.S. patent application Ser. No. 07/312,029, filed on Feb. 17, 1989 and entitled "Surgical Sponge." In as much as the present invention pertains to the manufacture of sponges such as described in assignee's copending application, this copending patent application is incorporated herein by reference.

The fabrication or manufacture of surgical sponges of the type described above and in assignee s aforementioned copending U.S. patent application was previously achieved by precutting a selected number of shaped sponge bodies of a particular size and shape from a roll of sponge material. These sponge bodies were then placed one at a time, by hand, over an anvil of an ultrasonic welder. The string was then placed, by hand, over the surface of the sponge body atop of the anvil and properly aligned under the horn of the ultrasonic welder to effect the bond between the string and the underlying sponge body. This "custom" fabrication of each surgical sponge was not only time consuming and expensive but lacked a desired level of repeatability and quality control. For example, the placement of the string over the sponge body required that each string be properly placed on each sponge surface under the horn of the welder and then maintained in this position without bends or wrinkles during the bonding process. This step of the bonding process introduced a quality control problem since it was difficult to properly place the string and maintain it in a proper orientation during welding which is necessary in order to assure that each surgical sponge possessed an adequate level of bonding between the string and the sponge body to be utilized in envisioned surgical procedure. The handling of the sponge body in the course of the prior art fabrication techniques also tended to disrupt the fibers of the body and promote linting during subsequent use of the surgical sponge. The practice of the present invention minimizes handling of the sponge bodies so that the integrity of the sponge web is better maintained.

SUMMARY OF THE INVENTION

It is a primary aim or objective of the present invention to provide a method and apparatus for the manufacture of surgical sponges, particularly neurosurgical sponges, in an automated and continuous manner. The present invention provides a significant improvement in production efficiency and quality control in the manufacture of medically acceptable surgical sponge over the heretofore utilized surgical-sponge manufacturing techniques, such as briefly described above.

Generally, the primary objective of the present invention is achieved in an apparatus which fabricates surgical sponges, each formed of a sponge body of a preselected width and length with at least a segment of a string attached to the surface thereof. Preferably the string is characterized by comprising material which is opaque to x-rays. The apparatus comprises structural support means; supporting means carried by the structural support means for supporting a supply of web of sponge body material (e.g. a rolled web or a fan folded web) of a length sufficient to form a plurality of sponge bodies; supporting means carried by the structural support means for supporting a supply of string (e.g. a spool of string); joining means carried by the support means for joining a segment of string displaceable from the string supply to a flat surface of the sponge body material adjacent to an outboard end thereof remote to the web supply supporting means; sponge severing means carried by the support means; string driving means for displacing string from the supply of string in one direction over a surface on the support means; sponge driving means for displacing sponge from the supply thereof over the work surface on the support means in a direction substantially perpendicular to said one direction and along a plane underlying the segment of string; drive means coupled to the joining means and the sponge severing means for alternately displacing the sponge severing means and the joining means in the direction substantially perpendicular to said one direction for sequentially positioning the sponge severing means over a selected length of the sponge displaceable from the sponge supply and the joining means over the segment of string; and means for sequentially receiving a plurality of sponge bodies serially coupled to one another by the string at longitudinally spaced apart locations. Bias means and string centering means are disposed at a location intermediate the joining means and the means for sequentially receiving a plurality of sponge bodies for maintaining a tensile loading on the string coupling the plurality of sponge bodies in said one direction.

Another object of the present invention is to provide for the automatic and continuous manufacture of surgical sponges of preselected widths and lengths with or without trailing string portions and utilizable for locating surgical sponges when packed deep into a body cavity.

The further object of the present invention is to provide for the separation of the sponge bodies serially connected by the string to form discrete surgical sponges in automatic and continuous manner. This object is achieved by using drive means for displacing string-connected sponge bodies from the joining means and the sponge severing means and then employing string cutting means for cutting the string extending between successive sponge bodies at a location contiguous to an edge of each sponge body of the plurality of sponge bodies.

Other and further objects of the present invention will become obvious upon understanding of the illustrative embodiments about to be described or will be indicated in the appended claims, and various advantages not referred to herein will occur to one skilled in the art upon employment of the invention in practice.

DESCRIPTION OF THE DRAWINGS

FIG. 1 is a schematic block diagram showing the general arrangement and step-by-step operation of the surgical sponge manufacturing apparatus of the present invention;

FIG. 2 is a plan view showing details of a preferred embodiment of the present invention with the sponge roll and sponge drive removed for showing details of the adjustable cam arrangement;

FIG. 2a is a plan view taken at arrow 2a in FIG. 2 and showing details of the sponge roll and sponge drive removed from FIG. 2;

FIG. 2b is a fragmentary sectional view taken along lines 2b of FIG. 2 for illustrating in greater detail the adjustable cam drive and the displacement compensator for the cam drive used for accurately displacing the carriage assembly;

FIG. 4 is an elevational view taken along line 4—4 of FIG. 3 at an angle turned 90 degrees from FIG. 3 and shows details of the carriage assembly together with the string spool, the driving arrangement for displacing the string, the welding and sponge cutting mechanisms on the carriage assembly, and the drive arrangement for string delivery of sponge bodies serially connected by the string to the sponge-string separating mechanism;

FIG. 4a is a fragmentary sectional view taken along line 4a-4a of FIG. 4 and illustrates details of the sponge trimming mechanism;

FIGS. 5, 6, and 7 show details of the welding and sponge cutting mechanisms in various positions relative to the string and sponge as achieved during the welding and sponge cutting operations.

Figure 3:
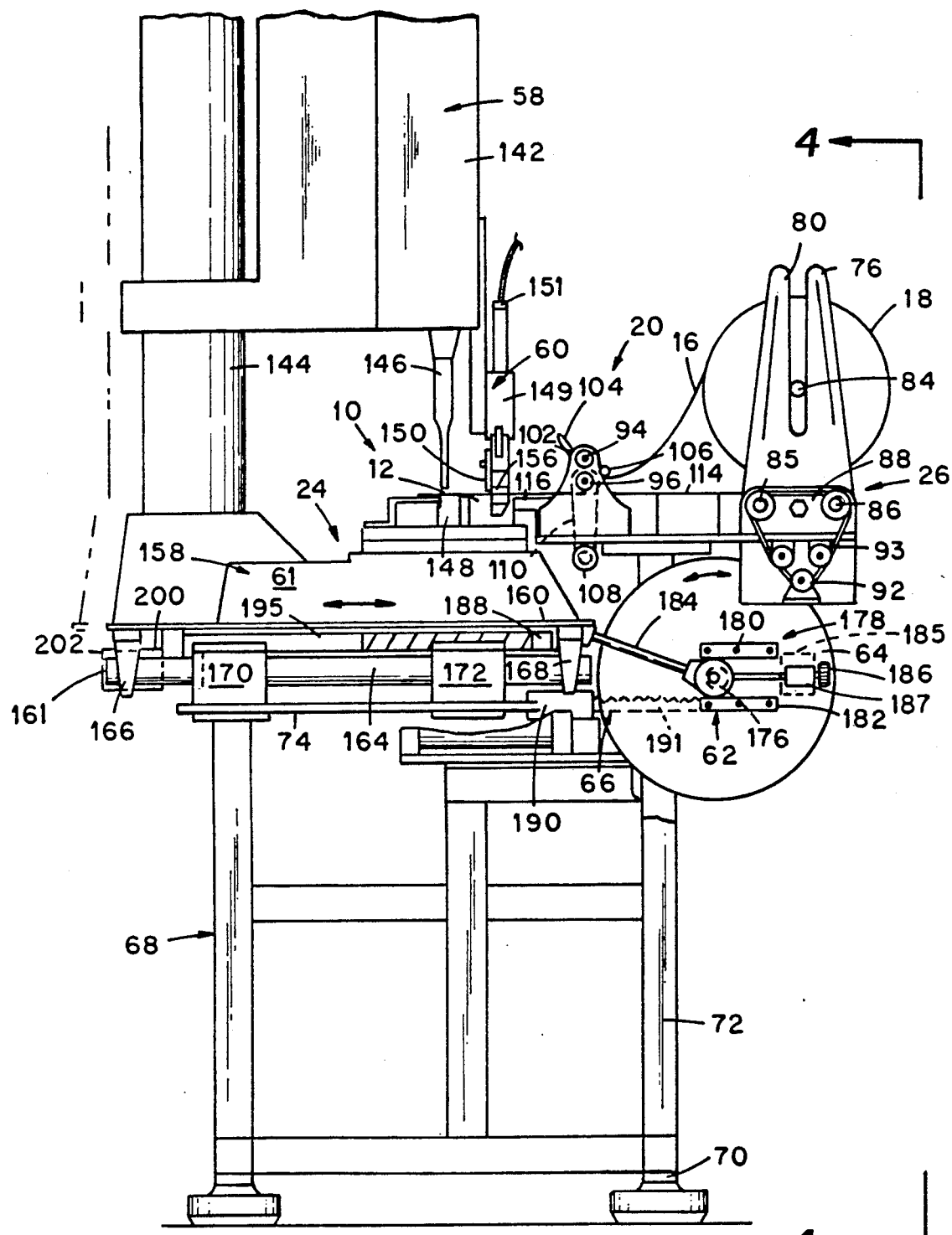
FIG. 3 is an elevational view, partly broken away, showing details of the carriage assembly and the sponge roll driving mechanism.
Figure 8:
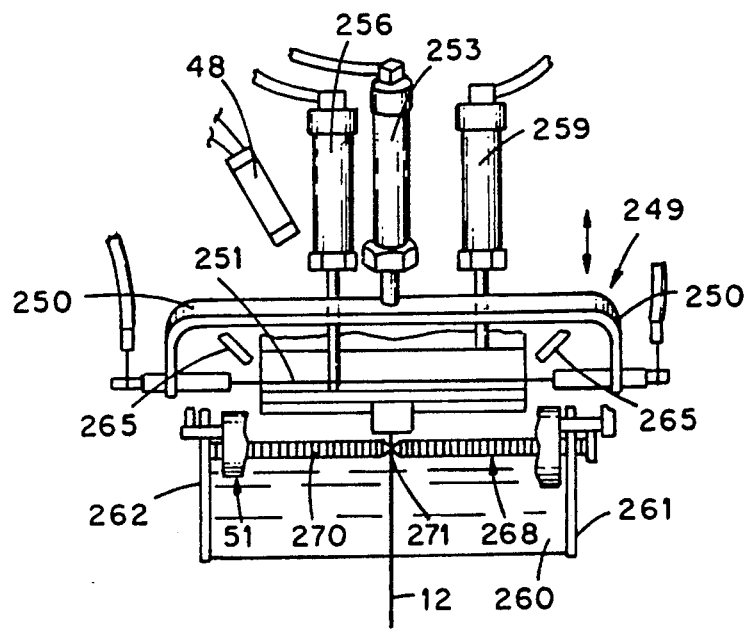
FIGS. 8 and 9 illustrate details of the mechanism utilized for separating the sponge bodies into discrete surgical sponges from a continuous line of sponge bodies serially connected by the string after emerging from the string-welding and sponge-cutting mechanisms.
Figure 9:
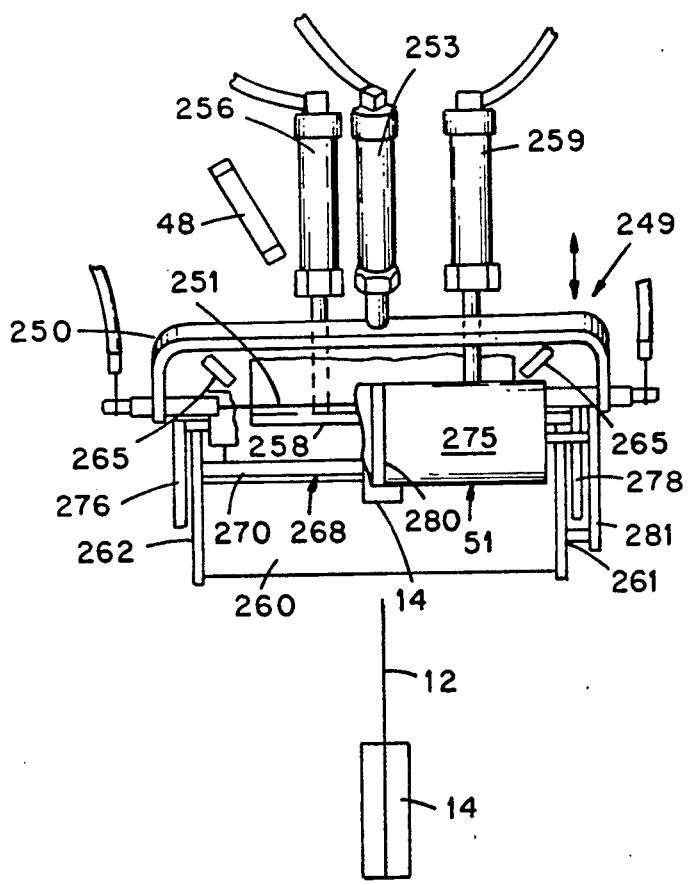

Preferred embodiments of the invention have been chosen for the purpose of illustration and description. The preferred embodiments are not intended to be exhaustive or to limit the invention to the precise forms disclosed. They are chosen and described in order to best explain the principles of the invention and their application and practical use to thereby enable others skilled in the art to best utilize the invention in various embodiments and modifications are as best adapted to the particular use contemplated.

DETAILED DESCRIPTION OF THE INVENTION

With particular reference to FIG. 1 of the accompanying drawings, there is schematically illustrated the surgical sponge manufacturing machine 10 in accordance with the present invention which is utilized for joining selected lengths of string 12, preferably containing x-ray opaque material, to sponge bodies 14 of preselected sizes in an automatic and continuous manner. In operation of this apparatus a strip of sponge 16 of selected width is fed from a sponge supply such as a sponge roll 18 through a sponge-feeding roller mechanism 20 which is driven by a suitable actuateable roller drive arrangement 22. This sponge strip 16 is fed onto a string-welding and sponge-cutting assembly 24 which supports an ultrasonic welder and a sponge shearing device, as will be described below. The width of the sponge roll 18 is of a preselected width in the range of about ¼ inch to about 6 inches. In order to accommodate sponge rolls of various widths, a sponge roll centering drive 26 is utilized to assure that the sponge roll is properly aligned at the center of the string-welding and sponge-cutting assembly 24. If the sponge strip 16 is provided by using a fan-folded supply of the sponge-forming web, a centering drive constructed substantially similar to the sponge roll centering drive may be utilized to align the sponge strip 16 taken from the fan-folded supply of web.

A spool 28 containing the string 12, which preferably incorporates x-ray opaque material such as described in assignee's aforementioned patent application, is stripped in selected increments from the spool 28 and passed through a string-feeder roller assembly 30 which is driven by a selectively actuated roller drive 32. The string extends through a string centering guide 34 and over an end segment or outboard end portion of the sponge strip 16 positioned on the surface of the welding and cutting assembly 24. This guide 34 is adjustable to permit optimal positioning thereof for accurately positioning the string 12 over the sponge strip in subsequent operation.

As shown, the string 12 and the strip of sponge 16 are driven in longitudinal directions perpendicular to one another so that the string 12 will intersect with the sponge strip 16 over the entire width thereof with an end portion of the sponge strip 16 of a selected length positioned under the string 12. The ultrasonic welder of the string-joining and sponge-cutting assembly 24 is actuated to bond the string 12 to the surface of the sponge strip 16. Upon completion of the joining of the string 12 to the sponge strip 16, the sponge strip 16 is severed at a selected location near the string 12 by the cutter of the string-joining and sponge-cutting assembly 24 to provide a sponge body 14 of the size desired of the surgical sponge product. As will be described in greater detail below, the sponge body 14 is preferably provided with a slight excess in length which, along with a short piece of string bonded thereto, is removed prior to completion of the surgical sponge product.

During the welding of the string 12 and cutting of the sponge strip 16, the portion of the string 12 extending beyond the welding and cutting assembly 24 is preferably confined or held down by a string hold-down mechanism 35 which inhibits a string bias or string tension applying mechanism 36 from exerting excess tension on the newly welded string prior to severing the sponge strip 16.

The string tension applying mechanism 36 may be of any suitable construction which is capable of providing a relatively continuous tension loading on the string 12 for maintaining the string 12 in a straight line on the sponge strip 16 for welding purposes and for storing variable lengths of string containing sponge bodies at spaced apart locations. Also, a string centering device 38 is preferably placed before or upstream of the string tension-applying mechanism 36 to cooperate with the guide 34 for maintaining the string 12 in proper alignment with the welder and sponge strip 16.

The unbroken string 12 contains sponge bodies 14 at spaced apart locations. This string 12, with the sponge bodies 14 thereon, is preferably conveyed from the string tension-applying mechanism 36, via a string centering device 40, into a sponge separating or string cutting assembly 42 which separates the serially connected sponge bodies 14 into discrete surgical sponges, each defined by a sponge body 14 coupled to at least a segment of a sponge locator string 12. Preferably, the string 12 extends or projects from the sponge body 14 a selected length in the range of about 10 to 14 inches. This string cutting assembly 42 preferably comprises a compressed belt drive 44 for feeding the string 12 bearing sponge bodies 14 into a sponge clamping and string cutting mechanism 46. Sensing means, such as a photocell 48, are positioned at the cutting mechanism 46 to determine the position of the leading end of edge of a sponge body 14 in the string cutting assembly 46 so that the belt drive 44 can be temporarily inactivated, the sponge clamped in place, and the string 12 severed at the leading edge of the sponge body 14. A small "excess" portion of the sponge body 14 and the section of string 12 attached thereto is also severed in the string cutting assembly 46 after the string 12 is cut to provide the sponge body 14 with a smooth end free of any raveling.

The finished surgical sponges are passed over a baffle 49 which is pivoted out in front of the path of the string 12 severing mechanism during the severing of the string for delivery of the finished surgical sponges into a suitable receptacle, not shown. A string centering device 50 and a driven roller 51 overlying and contactable with the string centering device 50 engage the string 12 trailing from a sponge body 14 discharged from the cutting mechanism 46 by the simultaneous operation of the belt drive 44, the string centering device 50, and the driven roller 51 for centering each succeeding sponge in the string cutting assembly 46, for expelling the surgical sponges from the apparatus and for facilitating the string cutting operation. This arrangement is useful for the manufacture of surgical sponges with a trailing string segment, such as in the case of neurosurgical sponges. However, the separation of surgical sponges without a trailing string segment can also be achieved by use of the sensor 48 to sequentially stop the belt drive 44 at each longitudinal end of the sponge body 14 so that the string can be severed at each edge of the sponge body 14 contacted by the string 12, thereby leaving no string portion extending beyond the perimeter of the sponge body 14.

The joinder or the welding of the string 12 to the sponge strip 16 is achieved in the string-joining and sponge-cutting assembly 24, preferably by an ultrasonic-type welder. With ultrasonic welding, a tenacious bond is provided between the string 12 containing thermoplastic material and the sponge body 14. In the present invention, the ultrasonic welder 58 is provided with a horn of a length essentially corresponding to the greatest anticipated length of the sponge body 14 to which the segment string 12 is joined. With selected length of an end segment of the sponge strip 16 positioned under the welding horn and under the string 12, the welder 58 is activated to join the string segment to the sponge strip 16 with the bonding occurring at essentially only the interface between the string 12 and the sponge material directly underlying the string 12.

When the string 12 is joined to the sponge strip 16, the string-joining and sponge-cutting assembly 24 is displaced as a single unit a selected distance in the direction away from the sponge roll 18 for forming sponge bodies 14 of relatively small widths or toward the sponge roll 18 for forming sponge bodies of relatively large widths (i.e., sponge bodies of widths greater than twice that of the fixed spacing between the horn of the welder and the sponge cutter) in order to place a selected portion of the sponge strip 16 under the sponge cutter 60. This displacement of the string-joining and sponge-cutting assembly 24 does not displace the string 12 or the sponge strip 16, but merely repositions the cutter 60 in the proper position over the sponge strip for cutting the sponge strip 16 to the specific length desired for the width of the finished surgical sponge. For the purposes of this description, the length of the sponge body 14 corresponds to the width of the sponge roll 18 while the width of the sponge body 14 is dictated by the preselected displacement of the sponge strip 16 by the sponge drive 26 and by the position of the sponge cutter 60 when displaced by the movement of the string-joining and sponge-cutting assembly 24. Upon completion of each cutting operation, the string-joining and the sponge-cutting assembly 24 is returned to the welding position for a subsequent welding operation.

The string-joining and sponge-cutting assembly 24 is reciprocatively displaced along a plane perpendicular to the direction of the movement of the string 12 and either away or towards the sponge roll 18. This assembly 24 includes a carriage or movable plate 61 for supporting both the welder 58 and the cutter 60. The carriage 61 is coupled to an adjustable cam arrangement 62 which includes a disk 64 rotatable by a rack and pinion drive 66. This cam arrangement 62 is selectively adjustable so as to provide the desired displacement of the string-joining and sponge-cutting assembly 24.

The operation of the apparatus of the present invention may be readily controlled by a suitable microprocessor (not shown) which is coupled to the various drives and sensors to provide the proper sequencing of the operational steps utilized in the manufacture of surgical sponges.

FIGS. 2-9 illustrate a preferred embodiment of the present invention which corresponds to the schematic arrangement illustrated in FIG. 1 where the sponge-bearing string 12 is conveyed to the string cutting assembly 42 for fabrication into discrete surgical sponges. As shown, the apparatus for manufacturing the surgical sponges as constructed in accordance with the present invention, comprises a support structure 68 having a base 70 of a generally rectangular configuration. The base 70 in provided with a braced, vertically extending framework 72 which supports a horizontal platform 74 for supporting the displaceable string-joining and sponge-cutting assembly 24.

The sponge roll 18 is supported on the platform 74 at an end portion thereof remote to the horizontal platform by a pair of vertically oriented plates or supports 76 and 78 which contain vertically extending slots 80 and 82 for receiving an axle or pin 84 of the sponge roll 18. The sponge supports 76 and 78 are movably supported on threaded rods 85 and 86. These threaded rods 85 and 86 are affixed to the platform 74 by flanges 87 and 88 and are provided with right- and left-handed threaded portions so that upon rotation of the threaded rods 85 and 86 the supports 76 and 78 move away from or approach the center of sponge roll 18 so as to assure that the sponge roll 18 will always be centered and properly aligned with the horn of the ultrasonic welder 58 and the cutter 60. The spacing between the supports 76 and 78 is preselected to correspond essentially to that of the length of the sponge body 14 desired of the finished surgical sponge, which length as briefly mentioned above, may be in the range of about ¼ inch to about 6 inches. The supports 76 and 78 may be readily positioned to the desired spatial location from one another by employing a simple pneumatic or electrical drive motor such as a DC stepping motor, generally shown at 92.

With the sponge roll 18 in place between the supports 76 and 78, the sponge strip 16 is fed onto the string-joining and sponge-cutting assembly 24 by utilizing a suitable sponge feeding mechanism, as generally shown at 20 in FIG. 1. Satisfactorily results have been achieved by feeding the sponge 16 with a roller drive assembly comprising vertically stacked rollers 94 and 96. The ends of these are mounted in suitable flanges 100 and 102 which are attached to the platform 74. The roller 94 is mounted in the flanges 100 and 102 in a manner which will permit vertical adjustment for facilitating the stringing of the sponge strip 16 through the roller assembly 20 in order to properly feed the sponge strip 16 onto the string-joining and sponge-cutting assembly 24. For example, a cam arrangement provided by an offset on the end of the shafts supporting the roller 94 in the flanges 100 and 102 may be utilized. Roller positioning mechanism or handle 104 is attached to roller 94 for operating the cam arrangements for vertically positioning the roller 94 with respect to the roller 96 so as to selectively loosen or tighten the roller 94 on roller 96 against the sponge strip 16 being passed therebetween. Also, a fixed, horizontally extending rod 106 carried by roller support flange 102 may be positioned at a location intermediate the rollers 94 and 96 and the sponge roll 18 for initially guiding the sponge strip 16 through the roller assembly 20.

The roller 96 is the drive roller and is utilized to rotate the roller 94 for displacing the sponge strip 16 towards the string-joining and sponge-cutting assembly 24. The roller 96 may be satisfactorily rotated by employing by a DC stepping motor generally shown at 108 through a belt drive 110. With this drive arrangement, the sponge strip 16 can be fed in an intermittent manner to advance a selected length of the sponge strip 16 at the distal end thereof a preselected distance beyond the center of the string 12 as determined by and which corresponds to one-half the width desired of the sponge body 14 of the finished surgical sponge. The operation of the sponge feeding roller assembly 20 is initiated after each sponge body 14 is severed from the sponge strip 16 so as to place a further segment of the sponge strip 16 at the preselected distance beyond the intersection with string 12.

As best shown in FIG. 2a, a horizontally positioned plate 114 is affixed to and above the platform 74 for supporting the sponge strip 16 passing between the sponge roll 18 and the roller assembly mechanism 20. A further horizontally disposed plate 116 is cantileveredly mounted on platform 74 for supporting the sponge strip 16 at a proper level for the feeding onto the string-joining and sponge-cutting assembly 24.

With reference to FIGS. 2-4, the spool 28 of string 12 is supported on a vertical rod 118 attached to a plate 120 carried by the framework 72, preferably at a location underlying the level of the string-joining and sponge-cutting assembly 24 in order to facilitate the stripping of the string 12 from the top of a cone-shaped spool as generally shown at 28. The plate 120 preferably extends outwardly from the support structure 72 for placing the spool 28 of string 12 in a readily accessible position. The string 12 is stripped from the spool 28 by employing a drive assembly 30 which is shown comprising a pair of vertically stacked rollers 122 and 124 supported by flanges 126 and 128 attached to a horizontal plate 129 supported by legs 130 at a location in a horizontal plane common with the upper surface of the string-joining and sponge-cutting assembly 24 and above the platform 74. The lower roller 124 is the drive roller for displacing the selected length of string 12 from the spool 28 that is required for each surgical sponge. As the roller 124 is rotated and displaces string 12 from the spool 28, the string tensioning device 36 simultaneously pulls the string 12 across the string-joining sponge-cutting mechanism 24 and maintains the string 12 in tension for facilitating the welding of the string onto the underlying sponge strip 16, as will be described in greater detail below.

Like the drive for the sponge roll 18, the drive for the roller 124 may be provided by a DC stepping motor 131 coupled to the roller 124 by a belt drive 132. The upper roller 122 is provided with a suitable vertical adjusting mechanism such as a simple offset at the end of the shaft supporting the roller 122 in the vertical flanges 126 and 128. This cam-like adjustment of the roller 122, as provided by the operation of handle 134, is used for vertically positioning the upper roller 122 to facilitate the passing of the string 12 through the rollers 122 and 124 for the subsequent displacement of the string 12 from the spool 28 by the rotation of the rollers 122 and 124. The DC stepping motor 131 is intermittently operated to strip a preselected length of string 12 from the spool 28 for delivery of the string 12 to the string-joining and cutting-assembly 24. Before reaching the string-joining and sponge-cutting assembly 24 the string 12 is preferably passed through the adjustable string aligning fixture 34 provided by a vertical plate 138 with a string-receiving v-shaped notch 140 in the upper edge thereof. This string aligning fixture 34 is selectively adjustable to maintain the string 12 in alignment with the horn of the welder 58 when it is overlying the string 12 in the welding position. As briefly described above, the string 12 is initially passed through the string tension applying mechanism 36 and string centering device 38 in order to place sufficient tension on the string 12 to keep it straight while maintaining it in a desired position over the sponge strip 16 to permit accurate welding of the string 12 to the sponge strip 16.

As shown in FIGS. 3 and 4, the ultrasonic welder utilized in the practice of the present invention is shown comprising a housing 142 attached to a vertical support 144. The housing 142 is provided with a vertical displaceable horn 146 which overlies an anvil 148. The horn 146 of the ultrasonic welder 58 is of an elongated, relatively narrow rectangular configuration. The horn 146 is of a sufficient width to contact the full width of the string 12 to properly weld the string 12 to the underlying sponge strip 16 without overheating the sponge material adjacent to the point of contact with the string 12. The horn is also of a length adequate to assure that the full length of the segment of the string 12 overlying any envisioned size of sponge strip 16 is joined to the sponge strip 16. An ultrasonic welder suitable for the practice of the present invention is commercially available and identified as the "Branson Ultrasonic Welder No. 910M" which is available from Branson Sonic Power Company, Danbury, Conn.

The vertical displacement of the horn 146 onto the string 12 is utilized to apply an energy loading in the range of about 10 to 270 joules on the string 12 by the transmission of ultrasonic waves through the horn for a duration in the range of about 50 to 900 msec. This energy loading adequately heats the string 12 to cause it to become sufficiently molten to fuse to the underlying sponge strip 16 and thereby provide a tenacious bond therewith as described in detail in assignee's aforementioned patent application. These operational values are selected depending upon the size of the sponge strip with the lower values in each range being employed with the smaller sponges, e.g., $\frac{1}{4} \times \frac{1}{4}$ inch sponges, and with the higher values being employed with the larger sponges, e.g., $3 \times 6$ inch sponges.

In order to provide a sponge body 14 of a selected width, a segment of the sponge strip 16 is severed from the sponge roll 18 by employing a suitable shearing or cutting mechanism such as generally shown at 60. The cutter 60 is shown comprising a housing 149 containing a knife-like cutter or blade 150 coupled to the suitable drive such as an air cylinder 151 which is utilized for displacing the blade 150 over a shearing edge on the cutter housing 149. The housing 149 is provided with a rectangular passageway 156 for receiving the sponge strip 16 through the housing 149 so that the blade 150 may readily contact the underlying sponge strip 16. Also, the cutter 60 is preferably provided with a suitably actuated hold-down clamp (not shown) which bears against the sponge strip 16 to hold it in place while the blade 150 is shearing the sponge strip 16. Satisfactory results have been achieved by employing a commercially available cutting unit identified as "Sur-Cut No. SC-6 Knife" available from Azco Corp., Emerson, N.J. 07630.

As illustrated in the accompanying drawings and described herein, the cutter 60 is utilized for forming sponge bodies of rectangular configurations. However, it will appear clear that a different type of cutting mechanism may be utilized whereby sponge bodies of generally oval, circular or other configurations may be formed without departing from the spirit and scope of the present invention. For example, a cutter assembly with opposed convex cutters may be utilized to simultaneously form the trailing edge of the sponge body 14 to which the string 12 has just been joined and the leading edge of the next sponge body 14 to be welded to the string 12. With such an arrangement, a sponge body with an oval, circular, or other configuration may be readily provided even though the blades of the cutter may have to be preconfigured for each sponge size in order to provide it with the desired configuration.

With particular reference to FIGS. 3 and 4, the sponge cutting mechanism 60 is affixed to and supported by the welder housing 142 with the horn 146 of the ultrasonic welder 58 and the blade 150 of the cutter 60 positioned in a side-by-side relationship. The spacing between the narrow distal end of the welding horn 146 and the blade 150 of the cutter 60 is at least about two inches which is excessive for the formation of sponge bodies 14 of widths less than about four inches. For example, when manufacturing surgical sponges with a width of about one-fourth inch the cutter 60 must shear the sponge 16 at a location essentially one-eighth of an inch from the center line of welded string 12. However, since the horn 146 of the ultrasonic welder 58 must have adequate clearance from the sponge cutter 60 in order to be vertically displaced to form the weld, the sponge cutter or shearing unit 60 can not be positioned or mounted sufficiently close to the horn 146 of the welder 58 to shear the sponge strip 16 at the required location and still allow the horn 146 the necessary clearance for effecting the weld. Thus, in accordance with the present invention, the desired positioning of the ultrasonic welding horn 146 over the string 12 during the string welding operation and then the subsequent positioning of the cutter blade 150 over the proper location on the sponge strip 16 is achieved by mounting the ultrasonic welder 58 and the sponge cutting assembly 60 together side-by-side on a displaceable carriage or moveable plate 158. This carriage 158 is displaceable in a direction substantially perpendicular, preferably as near to perpendicular as possible, to the direction of string 12 movement and parallel to direction of displacement of the sponge strip 16 from the sponge roll 18. After the string 12 is welded to an end segment of the sponge strip 16, the carriage 158 is displaced a preselected distance away from the sponge roll 18 to, in effect, move the welder 58 out of the way of the cutter 60 while positioning the cutter blade 150 of the cutter 60 on the sponge strip 16 at the proper location for shearing the sponge strip 16. During the displacement of the carriage 158 with the cutter 60 and welder 58 supported thereon, the string 12 and sponge strip 16 connected thereto remain in a fixed position. Thus, the cutter 60 is moved relative to the sponge strip 16 for effectively placing the cutter 60 in the preselected position on the sponge strip 16 for cutting the sponge strip 16 and thereby forming a sponge body 14 of the desired width. The welder 58 and the cutter 60 which is fixed to the welder housing 142 are displaced as a single unit on the carriage and give way to one another during their distinct operations. Upon completion of the sponge cutting operation, the carriage 158 is then returned to the weld position for the next string welding operation.

The carriage 158 is shown comprising a rectangular plate 160 mounted on suitable slide arrangement 161. A satisfactory slide, as best shown in FIG. 2, may be formed of a pair of parallel coextensive rods or ways 162 and 164 which are affixed at opposite ends thereof to the underside of the carriage 160 by flanges 166 and 168. These rods 162 and 164, in turn, extend through and are supported by a pair of open cylinders 170 and 172 which contain suitable sleeves or bearings for facilitating low-friction movement of the carriage 158. These cylinder pairs 170 and 172 are shown attached to the horizontal platform 74 at longitudinally spaced-apart locations for permitting adequate room for the carriage to be reciprocatively displaced in accordance with the required positioning of the sponge cutter 60.

The displacement of the carriage 158 on the slide arrangement 161 may be achieved in any suitable manner such as by using fluid servos, screw drives, rack and pinion drives, and the like. A satisfactory and very rapid mechanism found to accurately displace the carriage 158 precise distances, and which can be readily adjustable for effecting selected displacements of the carriage 158, is an adjustable cam drive generally shown at 62. This cam drive is shown comprising a vertically oriented disk or wheel 64 positioned at a location within the framework 72 underlying the platform 74. The disk 64 is rotatably supported on the framework 72 in a bearing mount 174 by a horizontally oriented shaft 176 affixed at the center of the disk 64 on one side thereof. On the other side of the disk 64 opposite the shaft 176 is a slide arrangement 178 which may be suitably constructed of two parallel and elongated slides or ways 180 and 182 disposed at spaced apart locations for receiving a movable base portion of the cam therebetween. The slide 178 extends radially outwardly from the axis of rotation of the disk 64 towards the periphery of the disk 64. A rod or crank 184 is positioned in the slide 178 between the ways 180 and 182 and is selectively moveable within the ways 180 and 182 in either radial direction from the rotational axis of the disk 64 for selectively varying the radius about which the crank 184 travels about the axis of rotation of the disk 64.

As best shown in FIG. 2b, the selected displacement of the crank 184 in the slide 178 may be satisfactorily achieved by using a D.C. stepping motor-worm gear reducer arrangement 185 which drives a chain 186 threadedly coupled in a worm drive like arrangement to an elongated adjusting screw carried in a suitable housing and 187 attached to the base of the crank 184 in the ways 180 and 182. The opposite end of the crank 184 is provided with a clevis-like end 188 supported by a pin or bolt 189 between horizontally slotted plates 190 attached to and vertically extending from the underside of the carriage 158. The carriage 158 is displaced on the slide 161 by the movement of the crank 184 when the disk 64 is rotated. The crank 184 is moved radially at a right angle to the rotating axis of the disk for varying the stroke or the radius of crank travel about the rotational axis of the disk 64. The extent of rotation of the disk 64 used for the displacement of the carriage 158 in either direction is provided by alternately rotating the disk 64 180 degrees in opposite directions. This 180-degree revolution of the disk 64 in alternate directions may be readily provided by employing a pinion gear 192 coupled to the shaft 176 of the disk 64 with a rack gear 191 driven by an air over oil cylinder 193. The 180-degree revolution of the disk 64 corresponds to twice the length of the crank 184. In a typical construction of the machine of the present invention, the centerline of the welding horn 146 is at a fixed distance, say, two inches, from the cutting blade 150 of the cutter 60. Thus, in order to manufacture a surgical sponge one-fourth of an inch wide, the blade 150 of the cutter 60 must be moved to within one-eighth of an inch from the center of the string 12 since the other half of the sponge is on the other side of the string 12. This required positioning of the blade 150 necessitates a carriage travel of one and seven-eighths inches. This extent of carriage travel is achieved by providing the crank 184 with a length of fifteen-sixteenths of an inch on the disk 64.

The welder 58 must be returned to the weld position overlying the string 12 regardless of the distance the carriage 158 travels for positioning the cutting blade 150 at the selected position on the sponge strip 16 for the sponge-cutting step. It was found to be necessary to compensate for the distance the horn 146 of the welder 58 was moved from the centerline of the string 12 during the adjustment of the cam 62 as required for providing a different sized sponge in order to return the welding horn 146 to a location overlying the centerline of the string 12 for the next welding operation. This compensation for the displacement of the carriage 158 by the crank 184 may be provided by using a compensating screw 195 which is mounted on the underside of the carriage 158 and extends essentially the full longitudinal length thereof. The compensating screw 195 is threadedly coupled at one end thereof to a threaded yoke 196 which is attached to the clevis 188 by the pin 189 and is supported between the slotted plates 190. The other end of the compensating screw 195 is connected to the output shaft of a suitable speed reducer 200, such as a worm gear, which is also mounted on the underside of the carriage 158 adjacent to the end of the carriage remote to the crank 184. The speed reducer 200 and the compensating screw 195 may be suitably driven by a DC stepping motor 202 mounted on the housing of the speed reducer 200 and connected to the reducer 200 by a suitable coupling such as a timing belt and pulley arrangement (not shown). The reducer-supported compensating screw 195 and the threaded yoke 196 provide a selectively movable journal in the horizontal slots in the plates 190 for coupling the carriage means 158 with the crank 184 for moving the carriage 158 through the attachment of the speed reducer 200 affixed to the carriage 158. By employing the compensating screw arrangement, the effective length of the crank 184 can be selectively adjusted while concurrently positioning the carriage 158 for maintaining the carriage 158 in a selected position where the welding horn 146 overlies the string 12. Thus, if the radius of the crank 184 is changed while the welder 58 is in the welding position, the welder 58 without the use of the compensating screw arrangement would normally be out of position over the string 12 when the carriage 158 is returned from the cutting position to the welding position by the cam 62. However, by using the compensating screw arrangement the carriage 158 is positioned to assure that the welder 58 is brought back to the centerline over the string 12.

The particulars relating to the setting of the length of the crank 184 at the disk 64, and compensation required by the use of the compensating screw arrangement for each width of the sponge can be readily predetermined so that the set-up of a suitable micro-processor used for operating the various components of the machine of the present invention can be utilized for effecting essentially automatic alignment of the welder 58 and the string 12 for each sponge size.

When the sponge strip 16 intersects and extends under the string 12 the preselected distance corresponding to one-half the width of the sponge body 14 and the carriage 158 is positioned for welding the string 12 to the sponge strip 16, the string 12 is clamped in position by the string hold down 35. This hold-down 35 is preferably provided by a solenoid or servo actuated rubber pad 203 carried by a suitable platform in the same plane as where the weld occurs and is positioned in a location between the string tensioner 36 and the welder 58 for preventing the string tensioner 36 from excessively pulling on a hot weld while the sponge strip 16 is still intact. As soon as the string 12 is welded to the sponge strip 16, the crank 184 is energized to move the carriage 158 for placing the sponge cutter 60 in the cutting position. The string hold-down clamp 35 is released after the cut is made through the sponge strip 16. Immediately thereafter, the string feed 30 strips a new length of string 12 from the spool 28 while the string tensioning device 36 pulls the just welded sponge body 14 away from the welding unit for positioning a new string segment provided by the string feeder 30 under the horn 146 of the welder 58. Also, as this welded sponge body is moved away from the welder 58, the sponge feed rollers 20 are energized to run a new segment of the sponge strip 16 into position under the moving string 12 for the formation of a new surgical sponge. Simultaneously, with this displacement of the sponge strip 16 and string 12, the carriage 158 is returned to the welding position with the horn 146 overlying the new segment of the string 12 for welding the string 12 to the sponge strip 16.

Besides pulling the string 12 containing sponge bodies 14 away from the welder 58, the string bias or tension device 36 is also utilized to maintain the string centered in a straight line, i.e., without wrinkles or bends, so as to enable the welding horn 146 to accurately contact essentially the full length of the string 12 contacting the sponge strip 16. The string tension device 36 should be of the type which is capable of maintaining various lengths of the string 12 in tension so that as the sponge bodies 14 are joined to the string 12 they can be moved from the string-joining and sponge-cutting assembly 24. The string tensioning device 36 should also be capable of storing several welded sponge bodies 14 interconnected by the string 12 for subsequent reception in the separation device 42 or a suitable storage receptacle such as a box. The string tensioning device 36 may be formed of a suitably biased roller which permits the movement of a roller for a selected distance while maintaining a predetermined tensile loading on the string 12. Satisfactory results have been achieved by employing a "dancer roll"-type mechanism which is capable of maintaining uniform tension on the string 12 as well as providing the desired sponge-body storage feature while maintaining various lengths of string 12 in tension. As illustrated in FIGS. 2 and 4, the dancer roll tension device 36 is provided by two spaced apart open channels 204 and 206 which vertically extend from a location on the framework 72 at a level generally corresponding to that of the anvil 148 to a location near the base 70. The particular length of the channels 204 and 206 should be such that sufficient storage of the string 12 with sponge bodies 14 attached thereto can be achieved for subsequent reception in the string cutting and separating assembly 42 while maintaining the string 12 in tension in the welding area. Normally, a channel length from about 12 to 36 inches is adequate for this purpose. In the string tensioning device 36, roller 208 is horizontally journaled on a shaft that extends between and is received in channels 204 and 206. A roller 212 is contacted by a dancer arm 210 which is pivotally secured at one end thereof to the vertical support structure 72. The dancer arm 210 contacts the small roller 212 disposed on the shaft at the end of the roller 208. In addition to the dancer-arm roller arrangement, free-rolling or idler gears 214 and 216 are positioned at both ends of the shaft meshing with a rack-like gear teeth 217 extending along the inside of the channels 204 and 206 for essentially the full vertical length of the channels to maintain the roller 208 in a horizontal orientation as it is vertically displaced in the channels 204 and 206. Another small roller is positioned on each end of the shaft to contact the channel leg opposite the rack gear to maintain proper meshing of the gear teeth with the rack. The string passing under the roller imparts rotation to the roller.

Upper and lower limit switches (not shown) may be disposed near the rotational axis of the dancer arm 210 for providing a control over the operation of the string-joining and the sponge-cutting assembly 24 and the string cutting device 42 depending on the supply of string 12 in the string tensioning device 36. The upper limit switch is used to temporarily inactivate the string cutting device 42 when an insufficient length of string 12 is present in the string tensioning device 36 for the operation of the string cutting device 42. The lower limit switch is used to temporarily inactivate the string-joining and sponge-cutting assembly 24 when an excess of string 12 is present in the string tensioning device 36.

A string centering device 38 is positioned at a location just prior to or upstream of the string tensioning device 36 while a further string centering device 40 is positioned at the point of string 12 exits from the string tensioning device 36. The upstream string centering device 38 is utilized along with the guide 34 to maintain the string 12 in its proper directional orientation under the welding horn 146. The string centering device 38 is shown comprising a rod 219 with left-and right-hand oriented threads and a small thread-free central portion 220. With this tread orientation the string 12 is fed by the thread contacted thereby toward the thread-free portion at the center of the centering device. The threaded rod 219 is horizontally mounted adjacent to the string inlet into the string tensioning device 36 and is rotated by a suitable drive motor 221 which becomes operative at the same time as the string feeder 30 is actuated to feed a new length of string 12 into the welding area.

The string centering device 40 is preferably of a construction similar to that of the string centering device 38 in that it contains a horizontally extending rod 222 with left- and right-hand threads and a thread-free portion 223 at the center of the threaded rod 222. A suitable drive motor 224 is coupled by a drive belt to the threaded rod 222 to rotate the rod 222 and center the string 12 at the thread-bare center portion 223 of the rod. The operation of the string centering device 40 is used in conjunction with the operation of the separation mechanism 42 so as to facilitate the movement of the sponge-bearing string 12 from the string tensioning device 36 in proper alignment with the separation device 42.

With particular reference to 2, 2a, 2b, 3, 4, 4a, 8, and 9, a preferred embodiment of the present invention utilizes the string separation device 42 wherein sponge bodies 14 interconnected by the string 12 are formed into discrete surgical sponges by cutting the string connecting each pair of string-joined sponge bodies 14. Excess sponge and the piece of the string segment attached thereto are trimmed from the leading end of the sponge body 14 to eliminate raveling of the sponge and string at the end of the sponge body 14. The string cutting assembly 42 may be a separate mechanism which can be selectively placed in an operating position with the surgical sponge fabrication machine 10, or preferably, is mounted on the base 70 of the support structure 68. The string cutting assembly 42 is preferably mounted on a suitable framework 228 vertically extending from the base 70 and supporting a horizontally disposed platform 229.

A string guide 230 is attached by a hinge arrangement 231 to the vertical framework 72 near the string centering device 40 and is utilized to guide the sponge bearing string 12 from the string tensioning device 36 to the belt drive 44 of the string cutting assembly 42. A channel 232 in the guide 230 disposed in juxtaposition to the belt drive 44 helps maintain the string 12 at the center of the belt drive 44.

The belt drive 44 of the string cutting assembly 42, comprises two elongated belts 234 and 236 maintained in tension and disposed in an elongated housing 238 supported on platform 229. These belts 234 and 236 are sufficiently wide to maintain therebetween the sponge bodies 14 of any width manufacturable by the present invention. The belts 234 and 236 are maintained in an abutting relationship with one another by a spring arrangement 241 affixed to the housing 238 and extending between the upper and lower sections 239 and 240 of the housing 238 for urging them towards one another. The belt 234 is rotated about rollers 242 and 243 while belt 236 is rotated about rollers 244 and 245. The upper and lower roller 242 and 244 are coupled together by a spur gear arrangement 246 so that both belts are driven in a common direction when the lower roller 244 is rotated by a suitable chain or belt drive through a clutch 247 and a continuous running motor and speed reducer 248. The operation of the clutch 247 is intermittent in a selected periodic manner to deliver the sponge-bearing string 12 to the string cutting device 46 only when there is sufficient string 12 in the string tensioning device 36 to allow for the feed of at least a full length of the string 21 attached to a single sponge body 14 to the string cutting device 46. The operation of the clutch 247 is controlled by the upper limit switch associated with the string tensioning device and by the photo cell 48 which disengages the clutch 247 when the string 12 and the sponge body 14 thereon are in the proper location within the string cutting device 42.

A string and sponge cutter mechanism 46 of the string cutting assembly 42 is attached to the housing 238. This cutting mechanism 46 includes a hot-wire cutter 249 which comprises a generally u-shaped arm 250 for holding opposite ends of a resistance-heated wire 251 in a horizontal plane overlying the interface between the belts 234 and 236. This u-shaped arm 250 is supported by a frame 252 which is attached to the housing 238 and coupled to a suitable pneumatic servo 253 supported by the frame 252 for effecting the vertical displacement of the hot wire 251. The pneumatic servo 253 is preferably provided with a suitable dashpot or the like (not shown) which is utilized to slow the descent of the hot wire 251 as it touches and passes through the string 12 to assure the severing of the string along with the searing and sealing of the string ends. In addition to the hot wire cutter 249, a servo operated sponge hold-down or clamp 254 and a servo operated sponge shearing or cutting device 255 are positioned intermediate the hot-wire cutter 249 and the housing 238 for trimming excess sponge and the short piece of string attached thereto from the sponge bodies 14. The hold-down clamp 254 and the sponge cutting device 255 are preferably of a construction similar to that of the above described cutting device 60 utilized for shearing the sponge strip 16 into the discrete sponge bodies 14. The blade 258 of the cutter 255 and the hold-down clamp 254 are disposed adjacent to the interface of the belts 234 and 236 for receiving the string 12 and sponge bodies 14 attached thereto.

When the string 12 with sponge bodies 14 welded thereon are driven by the actuation of the belts 234 to 236 to a point near the exit of the housing 238 where the photo-cell 48 is employed to sense the arrival of the leading end or edge of a sponge body 14. This sensing of the position of the sponge body 14 is used to interrupt the operation of the clutch 247 so as to permit the operation of the hot-wire cutter 249 to separate the string and then the trimming of excess sponge in the cutting device 254. The string 12 is burned apart by actuation of the servo 253 and the dashpot to drive the hot wire 251 onto the string 12. This "slow" burning of the string 12 leaves a seared and sealed end on the string to prevent raveling of the string. Upon completion of string severing operation the string 12 and the sponge body 14 attached to the other end of the string 12 are in a precut form desired of the surgical sponge product. These finished surgical sponges are discharged from the cutting mechanism 42 into a suitable container for subsequent packaging.

The excess of sponge body 14 normally corresponds to a sponge length of about one-sixteenth inch at the leading of the sponge body 14 near the just severed string 12 and is severed or cut by the actuation of the servo 256 which displaces the blade 258 of the sponge cutter 255. This piece of excess sponge severed from the sponge body 14 includes a short piece of string 12 which was welded to the piece of excess sponge. This severing of the excess sponge and string effectively minimizes or eliminates any raveling of sponge and string at that end of the sponge and also provides a smooth interface between the string and the sponge body 14 at the end of thereof. In order to effectively cut the excess from the sponge body, the sponge hold-down clamp 254 is actuated to clamp the sponge in place within the sponge cutter by the actuation of servo 259 at a time just prior to the severing of the sponge by the sponge cutter 255. Upon completion of the severing of the excess sponge from the sponge body 14, the sponge hold-down clamp 254 is lifted from the sponge body 14 by the servo 259.

A pivotable baffle plate 260 is preferably positioned at the discharge end of the housing 238 to facilitate the removal of the finished surgical sponges from the string cutting device 42. This baffle plate 260 is of an elongated arcuate configuration and is horizontally disposed in a plane essentially at the same level as the interface between the belts 234 and 236. The baffle plate 260 is attached to flanges 261 and 262 which are pivotally attached to the housing 238 by a hinge arrangement 263. The pivoting of the baffle plate 260 may be achieved in any suitable manner such as by the use of a servo, belt drive or the like. Just prior to the string severing step effected by the vertical displacement of the hot-wire cutter 249, the baffle plate 260 is pivoted in a longitudinal direction with respect to the direction of string movement away from a location contiguous to the string and sponge cutter 255 to make room for the vertical movement of the hot wire 251.

When the string 12 is cut and the hot wire 251 is moved upwardly away from the string 12 the baffle 260 is pivoted back to a location where an elongated edge thereof rests against or is contiguous to the frame of the sponge cutter 255. The sponge body 14 and the string 12 attached to the sponge body 14 that was just cut in the cutter 46 is then pushed out from between the belts 234 and 236 by the operation of the clutch 247 which in turn pulls a new string 12 and sponge 14 into the cutting area for the next string-cutting and sponge-trimming operation.

The baffle plate 260 allows for the finished surgical sponges to pass from the string cutter 46 into a suitable receptacle such as generally shown at 264 for the finished sponge bodies. Also, if desired, a pair of air jets as generally shown in 265 may be supported on the housing 238 and directed at a point centrally of the leading edge of the sponge body 14 at the interface between the string cutter 46 and the baffle plate 260 for facilitating the removal of the finished sponge body 14 away from the cutting area as the rotation of the belts 234 and 236 convey a new sponge body 14 into the cutting area of the string cutter 46.

To facilitate the delivery of a new sponge body 14 and string 12 attached thereto into the string cutting and sponge trimming area of the string cutter 46 and to assure that the sponge body 14 is in a proper alignment in the string cutter 46 for removing the excess sponge from the leading end of the sponge body 14, a string centering device 268 is preferably attached to the baffle support plates 261 and 262 at a location adjacent to and overlying the baffle plate 260. This string centering device 268 comprises a horizontally extending rod or screw 270 provided with left- and right-handed threads and a thread-free central portion 271. The string centering device 268, which functions in manner similar to the string centering devices 38 and 40, may be coupled to a suitable belt drive to the clutch 247 for concurrent operation with the belts 234 and 236. As a sponge body 14 is driven from the housing 238 by the operation of the belts 234 and 236, the string 12 trailing the sponge body 14 is aligned in the center portion 271 of the centering screw 270 to properly position the succeeding sponge body 14 in the sponge cutter 255. Also, when the sponge body 14 discharged from the sponge cutter 255 and the belt drive 44 passes over the baffle plate 260, the baffle plate 260 is again pivoted away from the housing 238 so that the hot wire 251 may be lowered onto and sever the string 12 of the previously cut sponge body 14. This movement of the hot wire 251 to a string cutting position is initiated as soon as the clutch 247 is disengaged.

As pointed out above, when the sponge body 14 and the string 12 attached thereto are passed over the baffle plate 260, the string centering device 268 is used to maintain the string 12 in a straight line in order to properly position the succeeding sponge body 14 in the cutter for the next string cutting and sponge trimming operation. In order to further provide for this straight-line feed of the string 12 and sponge bodies 14, as well as to facilitate the cutting of the string with the hot wire 251, a roller 275 is disposed in a fixed position over the baffle plate 260. The roller 275 is attached to the housing 238 by plates 276 and 278. The roller 275 is preferably provided with a centrally positioned raised section or an encircling conformable surface portion 280 for engaging the string 12. This conforming surface 280 on the roller 275 rests on the string centering rod 270 over the thread-free central portion 271 when the baffle plate 260 is pivoted away from the housing to allow the hot wire 251 to contact the string 12. The roller 275, like the string centering device 268, may be coupled by a suitable belt drive 281 to the clutch 247 for concurrent operation therewith. When this roller 275 contacts the string 12 in the string centering device 268 it holds the string 12 in position in the string centering device 268 for the hot wire 251 to descend and burn through the string 12. By centering the string 12, the string 12 can be readily severed by the hot wire 251 and also assure that the string ends provided by this cutting are properly fused and sealed to inhibit raveling. This roller 275 also serves to direct the sponge downwardly over the baffle plate 260.

In order to provide a more facile understanding of the present invention, a typical operation of a surgical sponge manufacturing procedure is set forth below. With particular reference to FIG. 1, string 12 from the spool 28 is initially fed over string-joining and sponge-cutting assembly 24 and through both the string tensioning device 36 and string cutting mechanism 42. With the string 12 in place and a tension loading applied to the string by the string tensioning device 36, the sponge strip 16 from the sponge roll 18 is delivered onto the string-joining and sponge-cutting assembly 24 and positioned so that an end portion of the sponge strip 16 extends under the center of the string 12 a distance corresponding to the one-half the width of the surgical sponge desired. With the sponge strip 16 in place, the welding of the string 12 of the sponge strip 16 is provided by vertically displacing the welding horn 146 to contact the string and heat the string 12 sufficiently to provide a fusion weld with the underlying sponge body.

During the string welding operation, the string hold-down clamp 35 is actuated to prevent the string tensioning device 36 from excessively pulling on the hot weld. Upon completion of the welding step, the adjustable cam system 62 is actuated to displace the carriage 158 supporting the welder 58 and the sponge cutter 60 a sufficient distance in a direction away from the sponge roll 18 for forming of sponge bodies 14 of relatively narrow widths and towards the sponge roll 18 for forming sponge bodies 14 of relatively large widths, i.e., of widths greater than about 4 inches. The movement of the carriage 158 is used to position the sponge cutter 60 over the sponge strip 16 at a location corresponding to one-half of the sponge width from the center of the string 12. The sponge strip 16 is then severed by the sponge cutter 60 and the string hold-down 35 is released. At this point, the string feed rollers 30 are actuated to feed a new length of string 12 into the string welder with this length of string being dictated by the length of string desired for the finished surgical sponge. Simultaneously with the feeding of the new length of string, the sponge roll drive 20 is actuated to feed a second length of the sponge strip 16 under the string 12 for next string welding operation.

As succeeding sponge bodies 14 are welded to the string 12 at selected spaced intervals thereon, the string 12 with the sponge bodies 14 are delivered through the string tensioning device 36 and into the belt drive 44. When a string 12 with a sponge body 14 is about to emerge from the sponge-clamping and string-cutting device 46, the presence of the leading edge of the sponge body 14 sensed by a photo-cell 48 and the belt drive 44 is momentarily inactivated. During the early stages of the displacement of the sponge body 14 through the belt drive 44, the baffle plate 260 is disposed in an abutting relationship with the sponge-clamping and string-cutting device 46 to guide a finished or previously trimmed sponge body 14 away from the belt drive 44 and the sponge-clamping and string-cutting device 46. When the previously finished sponge body 14 has sufficiently cleared the belt drive 44 and the sponge-clamping and string-cutting device 46, the baffle plate 260 is pivoted away from an abutting relationship with the sponge-clamping and string-cutting device 46. This pivoting of the baffle plate 260 places the string 12 connected to the previously finished sponge body 14 and the sponge body 14 being displaced in the belt drive 44 in the string centering device 50 and under the roller 51 for maintaining the string 12 in the center of the belt drive 44.

As the leading end of sponge body 14 being delivered by the belt drive 44 is sensed at the exit of the sponge-clamping and string-cutting device 46 and the belt drive 44 halted, the sponge body 14 is clamped in place. The hot wire 251 is then lowered against the string at or near the leading end of the clamped sponge body 14 to sever the string 12. The roller 51 acts with the string centering device 268 to center the string 12 while the hot wire 251 severs the string 12. Also, the pivoting of the baffle plate 260 moves the latter out of the path of the descending the hot wire 251. Excess sponge and the string portion 12 attached thereto is then sheared from the leading end of the sponge body 14 by the cutter 255 and discarded. The baffle plate 260 is then pivoted back into an abutting relationship with the sponge-clamping and string-cutting device 46 for receiving the just finished sponge body 14 thereon. This severing of the string 12 by the hot wire 251 completes the fabrication of the surgical sponge which, upon the pivoting of the baffle plate 260, allows for the finished surgical sponge to be discharged from the apparatus into a suitable receptacle for subsequent packaging. The aforementioned steps are sequentially repeated to provide the desired quantity of surgical sponges.

It will be seen that the present invention provides for the manufacture of surgical sponges of various types and configurations in an automated and continuous manner with a high level of quality control. The surgical sponges prepared by practicing the present invention are of high quality and possess sufficient structural integrity to assure that the sponges can be satisfactorily employed in any desired surgical procedure.

What is claimed is:

1. Apparatus for fabricating surgical sponges each formed of a sponge body of a preselected width and length with at least a segment of a string attached to a surface thereof, comprising support means, web supporting means carried by said support means for supporting a supply of web of sponge body material of a length sufficient to form a plurality of sponge bodies, string supporting means for supporting a supply of string, joining means carried by the support means for joining a segment of string displaceable from the supply of string to a surface of the web of sponge adjacent to an end thereof remote to the web supply, severing means carried by the support means and adapted to sever a length of web from said supply thereof, string driving means for displacing string from the supply of string in one direction over a surface on the support means, driving means for displacing the web of sponge body material over the surface on the support means in a direction substantially perpendicular to said one direction and along a plane underlying said segment of string, drive means coupled to the joining means and the sponge severing means for alternately displacing the severing means and the joining means a selected distance in the direction substantially perpendicular to said one direction for sequentially positioning the severing means over a selected length of the web displaceable from the supply of web and the joining means over said segment of string, and means for sequentially receiving a plurality of sponge bodies serially coupled to one another by the string at longitudinally spaced apart locations.

2. Apparatus as claimed in claim 1, wherein said means for sequentially receiving said plurality of sponge bodies comprises cutting means for cutting at least the string interconnecting the serially coupled sponge bodies to provide discrete surgical sponges.

3. Apparatus as claimed in claim 2, wherein bias means are disposed at a location intermediate the string joining means and said cutting means for maintaining a tensile loading on the string in said one direction.

4. Apparatus as claimed in claim 1, wherein bias means are disposed at a location intermediate the string joining means and said means for sequentially receiving said coupled severed sponge bodies for maintaining a tensile loading on the string in said one direction.

5. Apparatus for fabricating surgical sponges each defined by a sponge body of a preselected width and length and with at least a segment of a string joined to a surface portion of the sponge body, comprising support means, roll supporting means carried by said support means for supporting a roll of sponge of a length sufficient to form a plurality of sponge bodies, spool supporting means carried by said support means for supporting a spool of string, displaceable carriage means carried by said support means, welding means supported by the carriage means for joining a segment of string displaceable from the spool to a surface of the sponge at a selected location adjacent to an end thereof remote to the roll supporting means, sponge shearing means carried by the carriage means at a location intermediate the welding means and the roll supporting means for shearing the sponge to form discrete sponge bodies, string driving means for displacing string from the spool of string in one direction over a surface on the carriage means, sponge driving means for displacing a selected length of sponge from the roll of sponge over a surface on the carriage means in a direction substantially perpendicular to said one direction and under a segment of string on the carriage means to position said end of the sponge a selected distance from said segment of string, drive means for displacing the carriage means in the direction substantially perpendicular to said one direction for sequentially and alternately positioning the welding means over the segment of string for joining the segment of string to the sponge and positioning the sponge shearing means at a selected position over a preselected longitudinal length of the sponge displaceable from the roll of sponge for shearing the sponge at said position to provide a sponge body of preselected width, and means for sequentially receiving a plurality of discrete sponge bodies serially coupled to one another by the string at longitudinally spaced apart locations.

6. Apparatus as claimed in claim 5, wherein bias means are carried by the support means at a location intermediate said carriage means and said means for receiving a plurality of sponge bodies for providing a tensile loading on the string in said one direction.

7. Apparatus as claimed in claim 6, wherein said means for sequentially receiving a plurality of discrete sponge bodies comprises drive means for displacing sponge bodies serially coupled by the string from the bias means, and wherein string cutting means are disposed adjacent to the drive means for displacing the serially-coupled sponge bodies for cutting at least the string extending between successive sponge bodies at a location contiguous to an edge of each sponge body of said plurality of sponge bodies.

8. Apparatus as claimed in claim 5, wherein said string comprises thermoplastic material, wherein said welding means comprises an ultrasonic welder having vertically displaceable horn means overlying and contactable with said segment of string and adapted to sufficiently heat the segment of string to effect the joining of the segment of string to the sponge at a location thereon underlying the segment of string, and wherein said horn means longitudinally extend in said one direction and are of a length at least coextensive with the preselected length of the sponge disposed in said one direction and defining the length of each sponge body.

9. Apparatus as claimed in claim 5, wherein said sponge shearing means comprises an elongated vertically displaceable cutter extending in a direction parallel to said one direction, and wherein said means for actuating said sponge shearing means comprises drive means for vertically displacing the cutter to sever the sponge along a vertical plane extending in said one direction at said position.

10. Apparatus as claimed in claim 5, wherein said drive means for displacing the carriage means comprises adjustable cam means attached to the support means and coupled to the carriage means, and wherein adjusting means are coupled to said cam means for selectively adjusting the cam means to sequentially displace said carriage means selected distances for alternately positioning said welding means at a location where the welding means overlies said segment of the string or where said sponge shearing means are at said position on the sponge displaced from the roll of sponge.

11. Apparatus as claimed in claim 10, wherein said cam means comprises a disk rotatably supported by said support means for rotation about an axis, elongated slide means are carried by said disk and extend radially outwardly from said axis, elongated rod means are carried at one end thereof by said slide means and are coupled at an opposite end thereon to said carriage means, wherein said adjusting means selectively position said one end of the elongated rod means at a selected distance from said axis, and wherein drive means are coupled to said disk for sufficiently rotating said disk about said axis in alternate rotational directions for displacing said elongated rod means to effect the sequential displacement of said carriage means in alternate directions.

12. Apparatus as claimed in claim 11, wherein compensating means are coupled to the elongated rod means at said opposite end thereof for positioning said carriage means upon selective adjustment of the effective length of said elongated rod means to assure that the carriage means is returned to a position where the welding means sequentially overlies the string during alternate displacements of the carriage means by the drive means coupled to said disk.

13. Apparatus as claimed in claim 12, wherein said compensating means comprises threaded yoke means supported by said carriage means and attached to said elongated rod means, and wherein elongated screw means supported by said carriage means threadedly engage said yoke means for displacing said carriage means in a direction perpendicular to said one direction for selectively positioning the carriage means.

14. Apparatus as claimed in claim 13, wherein drive means are attached to the carriage means and are coupled to said elongated screw means for rotating the screw means in the yoke means to displace the carriage means a selected distance in said direction perpendicular to said one direction.

15. Apparatus as claimed in claim 11, wherein said drive means coupled to said disk comprises rack and pinion means carried by said support means and coupled to said disk for rotating the disk in alternate directions.

16. Apparatus as claimed in claim 5, wherein said roll supporting means comprises a pair of vertical plate means spaced apart from one another in said one direction, wherein the roll of sponge is carried by and is disposed between said plate means, and wherein adjusting means are coupled to said plate means and are moveable towards or away from one another in said one direction for selectively varying the space between said plate means for carrying therebetween the roll of sponge of a selected width corresponding to the preselected length of the sponge body to maintain the longitudinal center of the length of sponge displaced from the roll of sponge along a constant center line regardless of the width of the roll of sponge.

17. Apparatus as claimed in claim 6, wherein said bias means comprises elongated vertically oriented channel means, wherein horizontally disposed roller means are carried by said channel means and are vertically displaceable thereon, wherein the string interconnecting the sponge bodies is positionable about said roller means, and wherein means are contactable with said roller means for urging said roller means in a downward direction to apply with said roller means the tensile loading on the string in said one direction.

18. Apparatus as claimed in claim 6, wherein string centering means are carried by said support means at a location intermediate said carriage means and said bias means for maintaining the string oriented in said one direction.

19. Apparatus, as claimed in claim 18, wherein guide means are carried by said support means at a location intermediate the spool of string and said carriage means and are in registry with the string for maintaining the string oriented in said one direction.

20. Apparatus as claimed in claim 18, wherein means for clamping the string are carried by said support means at a location intermediate the carriage means and the string centering means.

21. Apparatus as claimed in claim 7, wherein said drive means for displacing the sponge bodies serially connected by the string comprises platform means, wherein elongated belt means of a length sufficient to contact a plurality of sponge bodies and the string disposed therebetween are supported by said platform means, and wherein drive means are coupled to said belt means for driving said belt means for displacing the sponge bodies serially connected by the string to said string cutting means.

22. Apparatus as claimed in claim 21, wherein said string cutting means are supported by said platform means and comprise means for severing the string at said location contiguous to an edge of each sponge body and means for shearing a portion of each sponge body and the string attached to said portion at a location contiguous to said edge, and wherein drive means are coupled to each of said means for severing the string and said means for shearing a portion of each sponge body and string attached to said portion for sequentially effecting the severing of the string and then the shearing of the portion of sponge and string attached to said portion.

23. Apparatus as claimed in claim 22, wherein said means for severing the string comprises displaceable wire means heatable to a sufficient temperature to burn through and sever the string upon being displaced into a contacting relationship therewith, and wherein the drive means coupled to the means for severing the string are coupled to said wire means for displacing the latter into the contacting relationship with the string.

24. Apparatus as claimed in claim 23, wherein plate means are pivotally supported on said platform means at a location adjacent to said means for severing the string for sequentially receiving thereon each of the sponge bodies and string joined thereto upon displacement from said string cutting means by said belt means, wherein said string cutting means are disposed at location contiguous to the pivotable plate means and said belt means, wherein string centering means are supported by said plate means for maintaining the sponge bodies and string attached thereto oriented in a common longitudinal direction as they are sequentially displaced through said string cutting means by said belt means, and wherein drive means are coupled to said plate means for pivoting the latter in said common longitudinal direction a sufficient distance away from said means for severing the string to permit contact between said wire means and said string.

25. Apparatus as claimed in claim 24, wherein roll means are supported by said platform means at a location overlying and in contacting relationship with said string centering means when said plate means are pivoted away from said means for severing the string, wherein drive means are coupled to said roll means and actuateable substantially concurrently with the belt drive means for rotating the roll means to maintain the string coupled to a sponge body being displaced from said belt means centered in said means for severing the string.

26. A method for sequentially and continuously fabricating surgical sponges each formed of a sponge body of a preselected width and length with a string of a length of at least as great as that of the sponge body fixed to a surface of the sponge body, comprising the steps of (1) longitudinally displacing a preselected length of string from a supply of string in a one direction, (2) longitudinally displacing a selected length of sponge from a supply of sponge in a direction substantially perpendicular to said one direction to a position intersecting with and underlying a segment of said string, (3) joining the string segment to a surface of the sponge underlying the segment of string at a selected location adjacent to a longitudinal end of the sponge, (4) severing a portion of sponge corresponding to said selected length and having the string segment joined thereto from the length of sponge remaining in the supply of sponge with the severed portion of sponge providing a sponge body of the preselected width, and (5) displacing the severed sponge body with the string segment attached thereto from said position while simultaneously displacing a further preselected length of string from the supply of string in said one direction to said position, and thereafter repeating steps 2 through 5 for forming a plurality of sponge bodies serially coupled to one another by the string at longitudinally spaced apart locations.

27. The method for sequentially and continuously fabricating surgical sponges as claimed in claim 26, including the additional step of collecting the coupled sponge bodies.

28. The method for sequentially and continuously fabricating surgical sponges as claimed in claim 26, including the additional steps of sequentially cutting the string coupling successive sponge bodies at a location contiguous to a longitudinal end surface of each sponge body for forming a plurality of discrete surgical sponges.

29. The method for sequentially and continuously fabricating surgical sponges as claimed in claim 28, including a further step of severing a longitudinal end portion of each sponge body and the portion of string joined thereto at a location adjacent to said longitudinal end surface of the sponge body subsequent to each cutting of the string at the location contiguous to the longitudinal end surface of the sponge body.

30. The method for sequentially and continuously fabricating surgical sponges as claimed in claim 26, including the additional step of maintaining a tensile loading on the preselected length of string in said one direction.

31. The method for sequentially and continuously fabricating surgical sponges as claimed in claim 26, including the additional steps of selectively varying the width of the supply of sponge for providing the preselected length of the sponge body, and maintaining the length of sponge from the sponge roll at a selected longitudinal center.

32. The method for sequentially and continuously fabricating surgical sponges as claimed in claim 26, wherein welding means are used for joining the string segment to the surface of the sponge, wherein shearing means are used for severing the sponge, wherein the welding means and the shearing means are supported by moveable carriage means, and including the additional step of alternately displacing the carriage means a selected distance in opposite directions in the direction substantially perpendicular to said one direction to alternately position the shearing means at a location overlying the selected length of sponge corresponding to said preselected width of said sponge and position the welding means at a location overlying the string segment.

33. The method for sequentially and continuously fabricating surgical sponges as claimed in claim 26, wherein the string comprises thermoplastic material, wherein the joining of the string segment to the sponge at the location underlying the string segment is provided by the steps of subjecting the string segment and the sponge underlying the string segment to an energy loading for heating the thermoplastic material to a temperature sufficient to effect a weld of the string segment to the underlying sponge in contact therewith.

34. The method for sequentially and continuously fabricating surgical sponges as claimed in claim 26, wherein the string is of a length substantially greater than the preselected length of said sponge body.

35. The method for sequentially and continuously fabricating surgical sponges as claimed in claim 26, wherein said string is characterized by comprising material opaque to x-ray radiation.

* * * * *